(12) United States Patent
Rucker

(10) Patent No.: US 10,842,986 B1
(45) Date of Patent: Nov. 24, 2020

(54) SINGLE-USE CAP

(71) Applicant: Hal Rucker, Hillsborough, CA (US)

(72) Inventor: Hal Rucker, Hillsborough, CA (US)

( * ) Notice: Subject to any disclaimer, the term of this patent is extended or adjusted under 35 U.S.C. 154(b) by 422 days.

(21) Appl. No.: 15/665,205

(22) Filed: Jul. 31, 2017

(51) Int. Cl.
*A61M 39/20* (2006.01)
*A61M 39/10* (2006.01)

(52) U.S. Cl.
CPC ............ *A61M 39/20* (2013.01); *A61M 39/10* (2013.01); *A61M 2039/1033* (2013.01); *A61M 2205/273* (2013.01)

(58) Field of Classification Search
CPC .................. A61M 39/20; A61M 39/10; A61M 2039/1033; A61M 2205/273; A61M 5/50
See application file for complete search history.

(56) References Cited

U.S. PATENT DOCUMENTS

2010/0050351 A1\* 3/2010 Colantonio ............... A61L 2/18
15/104.93
2011/0217212 A1\* 9/2011 Solomon ............. A61M 39/162
422/292

\* cited by examiner

*Primary Examiner* — Brandy S Lee
(74) *Attorney, Agent, or Firm* — intellipat; Edward W. Scott, IV

(57) ABSTRACT

A single-use cap comprising a cap for connecting to an inlet or outlet of container, connector or port for accessing a material and a piston movably mounted inside the cap. The single-use cap further comprises a first retainer for temporarily holding the piston at a first unused position with respect to the cap. It also has a state converter for converting the piston from the first unused to a second used state when the single-use cap is used to connect to the outlet of the container, connector or port. Once the single-use cap is disconnected from the outlet of the container, connector or port, then a second retainer is activated for permanently retaining the piston in the second used state. The second used state prevents the single-use cap from being reused for connecting to the outlet of the container, connector or port. The second used state causes the piston to block a means for connecting the single-use cap to such an inlet or outlet of container, connector or port, in some instances, such as threads that mate with the container, connector or port.

6 Claims, 15 Drawing Sheets

SINGLE-USE CAP

FIELD OF THE INVENTION

The present invention is related to the field of caps for containers, connections or other purposes which are tamper-evident and discourage or prevent unauthorized usage.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Treatment of chronic medical conditions such as infection, vasculitis, renal failure or cancer often requires that patients have intravenous access catheters commonly known as "central lines" inserted to administer medications, infusions, fluids, liquid nutrition and the like. (Herein, collectively, the term "infusion" includes these cases. Intravenous means inside a vein.) These hollow tubes, or catheters, come in a variety of lengths and styles. Some catheters are long enough to reach nearly to the heart. However, their purpose is generally similar: to administer fluids, medications, or nutrition into the large veins of the body over a prolonged period of time.

These central venous catheters can remain in place on the patient's body for weeks or months. The advantages of these devices include: (1) high volumes of fluid may be administered into large central veins; (2) they may remain in place between giving the infusions, therefore obviating the need for frequent line changes; and (3) they often allow the patient to be discharged from the hospital to home or an alternate care facility (e.g., nursing facility and the like) which makes for less costly and more convenient care.

Although physicians often discharge patients out of the hospital with a central venous catheter in place, they or their staffs sometimes worry that persons with a history of administering illicit medications into their veins (intravenous drug abusers) will use the catheters to give themselves narcotics or other drugs. This central line abuse could cause contamination of the line and infection in the patient. In addition, administration of a high dose of the illicit drug directly into a central vein could cause overdose and possibly death. Therefore hospitals often keep these patients in the hospital for weeks past the time when they could otherwise be discharged to a less expensive care facility or home just to prevent abuse of the catheter. The catheters are not locked and therefore could be used for injection by the patients when they are at home not being observed. Prolonged hospital stays to deter potential abuse of installed catheters dramatically increase the costs of providing care and take up limited resources. Some patients may attempt to introduce unauthorized substances into these devices even when they are not discharged and stay in the hospital for treatment.

In recognition of some of these risks, many catheters now come with a protective sliding clip. This flat plastic part has a tear-shaped cutout that pinches the line shut to help prevent unwanted infusions. The clip can slide open accidentally and can be easily manipulated by the patient or others who are not medically qualified or authorized to access the lines. When it is surreptitiously opened, it can be closed again without any evidence of tampering. This device therefore lacks security and does not show any telltale signs that someone has tampered with it.

Different types of ports and connectors are typically located at the open end of catheters. These catheter ports include, but are not limited to, male Luers, needleless connectors, open female Luers, and hemodialysis connectors.

Catheters also often can be closed with caps that attach to the catheter port to cover and seal the line from contamination by foreign material. Like the sliding plastic clip however, the cap provides no prevention or evidence of tampering by unauthorized persons, and the catheter can still be used for unauthorized and dangerous purposes. There therefore exists a need for means for deterring and detecting unauthorized usage and access to catheter lines.

SUMMARY

A single-use cap comprising a cap for connecting to the inlet or outlet of container, connector or port for accessing a material and a piston movably mounted inside the cap. In embodiments of the present invention, the single-use cap is a catheter port protector, and the inlet or outlet of container, connector or port is a port on a central catheter line. In embodiments of the present invention, the material is fluid which is administered during treatment sessions, such as medication or fluids for medical purposes, and the catheter port protector is used to cover the catheter port between administrations.

The single-use cap further comprises a first retainer for temporarily holding the piston at a first unused position with respect to the cap. It also has a state converter for converting the piston from the first unused to a second used state when the single-use cap is used to connect to the outlet of the container, connector or port. Once the single-use cap is disconnected from the outlet of the container, connector or port, then a second retainer is activated for permanently retaining the piston in the second used state. The second used state prevents the single-use cap from being reused for connecting to the outlet of the container, connector or port. In one embodiment, the second used state causes the piston to block a means for connecting the catheter port protector, such as threads on the catheter port protector which mate with threads on the catheter port.

In embodiments of the present invention, the first retainer comprises a tab on the piston and an edge on the cap which mates with the tab to retain the piston at the first unused state. Further, the state converter comprises a tab on the piston and a first (insertion) and second (extraction) slot on the cap which mates with the tab, the state converter moving the tab from the first slot to the second slot.

In embodiments of the present invention, the state converter of the single-use cap further comprises a rotator for imparting a rotational motion onto the piston to move the tab from the first slot to the second slot. The rotator further comprises a ramp on the cap and a pin on the piston which, when the piston reaches a first position relative to the cap, causes the pin to contact the ramp and translate an insertion motion into a rotational motion. The state converter further comprises a means for extending the piston when the single-use cap is uninstalled from the outlet of a container, connector or port and, for example, blocking the threads from connecting to the catheter port. In embodiments of the present invention, the lock further may comprise a tab on the piston and a pocket on the cap for mating with the tab.

BRIEF DESCRIPTION OF THE DRAWINGS

The novel features of the invention are set forth in the appended claims. However, for purpose of explanation, several embodiments of the invention are set forth in the following figures.

DETAILED DESCRIPTION

In the following description, numerous details are set forth for purpose of explanation. However, one of ordinary skill in the art will realize that the invention may be practiced without the use of these specific details. In other instances, well-known structures and devices are shown in form in order to not obscure the description of the invention with unnecessary detail.

A single-use cap and usage thereof is disclosed herein in embodiments of the present invention. Such a cap may be used to contain the access of materials, such as fluids, to or from a container, line or living being. A single-use catheter port protector is specifically described in embodiments of the present invention and is used to cover the outlet of a catheter port when the port is not in use. While the single-use port protector of embodiments of the present invention is shown and described in the present disclosure with reference to medical applications, other applications of single-use protectors, caps or tops are contemplated within the spirit and scope of the present invention. Such applications may include, but not be limited to, providing single-use storage and access to materials such as foodstuffs, chemicals or other products. For the purposes of this disclosure, the teachings of the single-use catheter port protector of embodiments of the present invention (hereinafter "the port protector") are equally applicable to single-use caps.

A single-use port protector in embodiments of the present invention is usually installed at the time when the catheter is still attached to a patient, but whenever the catheter is put into an idle state thereby preserving the connection for later access. Upon removal of a properly installed port protector from the catheter port, the port protector enters a used state where it cannot be used again. The port protector in its used state is also tamper-evident since it cannot be put back onto the port, and if available for inspection, can also indicate removal. Usage of this port protector by medical personnel upon completion of administration of medication may discourage tampering of the catheter port end by unauthorized persons and may aid medical personnel in ascertaining whether some medical intervention is required, such as hospitalization to prevent further abuse or testing for infection.

The operation of the port protector of the present invention is shown and described with reference to FIGS. 1-3, for example, when medical personnel have completed administering medication. Of particular note is that personnel can properly install the port protector of these embodiments without any special tools as is sometimes required in prior art tamper-evident or single-use caps, such as those used for various medication and food products.

Figure 1:
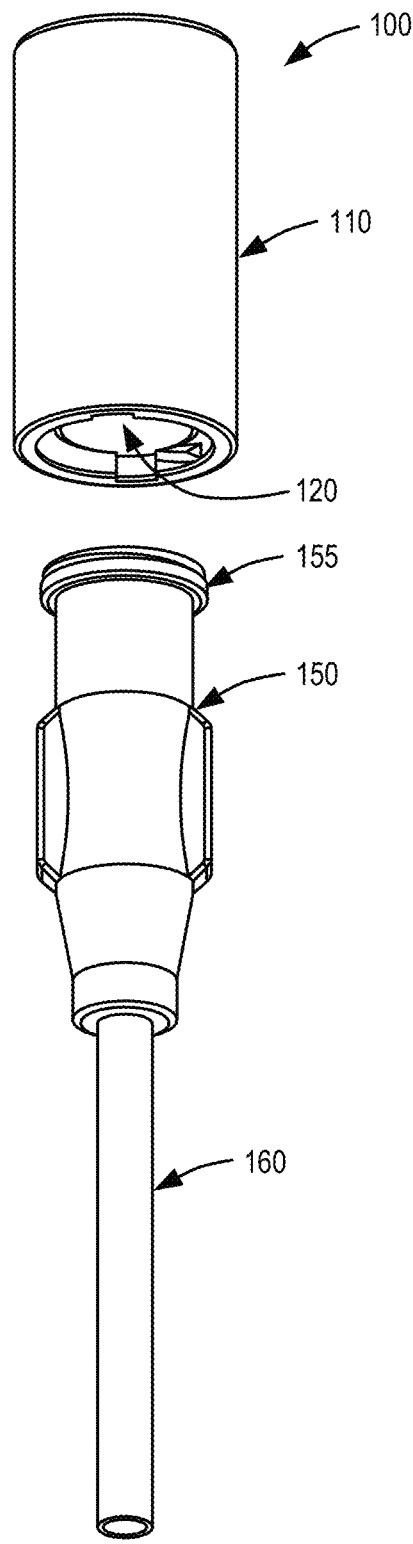
FIGS. 1-3 show the operation of a single-use catheter port protector in embodiments of the present invention.

FIG. 1 shows a single-use catheter port protector 100 of an embodiment of the present invention in its unused state, that is, prior to connection to the catheter port 150 of catheter line 160. The port protector 100 comprises two portions, which are visible in the figure a cap 110, and piston 120. In embodiments of the present invention, cap 110 and piston 120 are comprised of a sufficiently rigid yet flexible thermoplastic material, such as medical grade Delrin, to provide some spring functionality and which is safe for usage in medical applications. Other materials may be selected according to application, such as food-safe plastics. These components can be manufactured by any number of known manufacturing techniques such as injection molding, 3-D printing, casting or CNC machining.

The cap 110 encloses and captures piston 120. Piston 120 is movable inwardly and is shown in the catheter port protector 100 in its unused state and is locked from moving outwardly relative to the cap 110 in a slightly recessed manner prior to installation. This allows easy installation by threading cap 100 onto catheter port 150. Catheter port 150 typically has a threaded end 155 which mates with a prior art cap in the prior art. In embodiments of the present invention, 155 mates with a threaded portion of the catheter port protector 100 and can be used for covering the catheter port 150 when the catheter port 155 is not in use.

Figure 2:
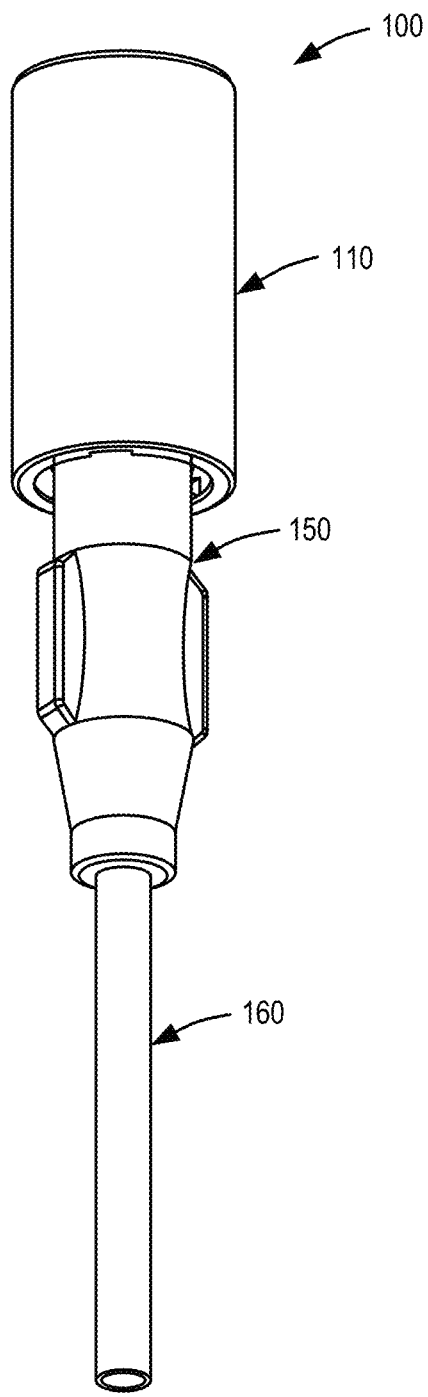

FIG. 2 shows port protector 100 when it has been installed on the end of catheter port 150. In this instance, the operator (e.g. a clinician), inserts catheter port 150 into the end of port protector 100 and rotates the threaded portion 155 so that it mates with a complementary threaded portion of port protector 100. The port protector 100 thus covers the catheter port 150 as shown in the figure.

Figure 3:
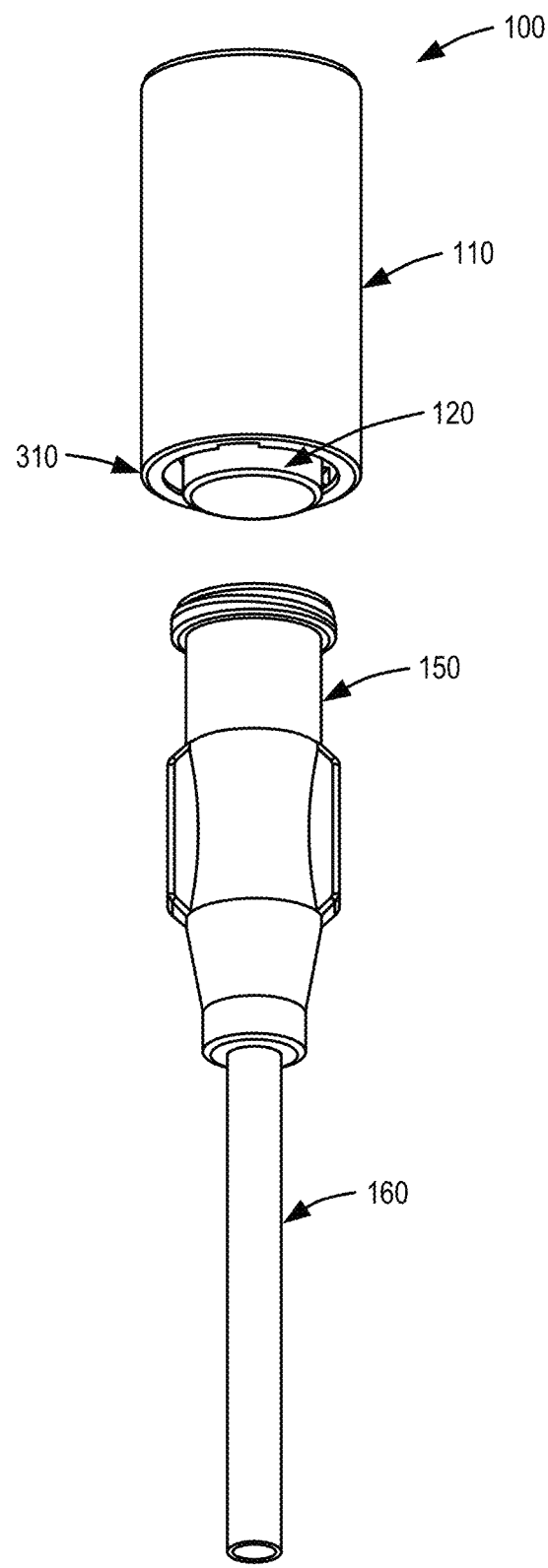

FIG. 3 shows the state of port protector 100 when it is removed from catheter port 150. After installation, the port protector 100 may be unscrewed and removed from catheter port 150. When the port protector 100 is removed from catheter port 150, by operation of embodiments of the present invention, the piston 120 then automatically extends beyond the edge 310 of cap 110. Piston 120 then locks into this extended position in embodiments of the present invention. Because of this locked position extending beyond the edge of the cap, port protector 100 can no longer be threaded onto catheter port 150 and is prevented from being used again. It is therefore can only be used once it is single-use. The locked extended position of piston 120 also indicates that the catheter port cap 100 has been removed from the catheter port 150 subsequent to installation. The port protector is therefore also tamper-evident, that is, it will indicate that it has been removed, such as by unauthorized personnel for unauthorized purposes.

Figure 4:
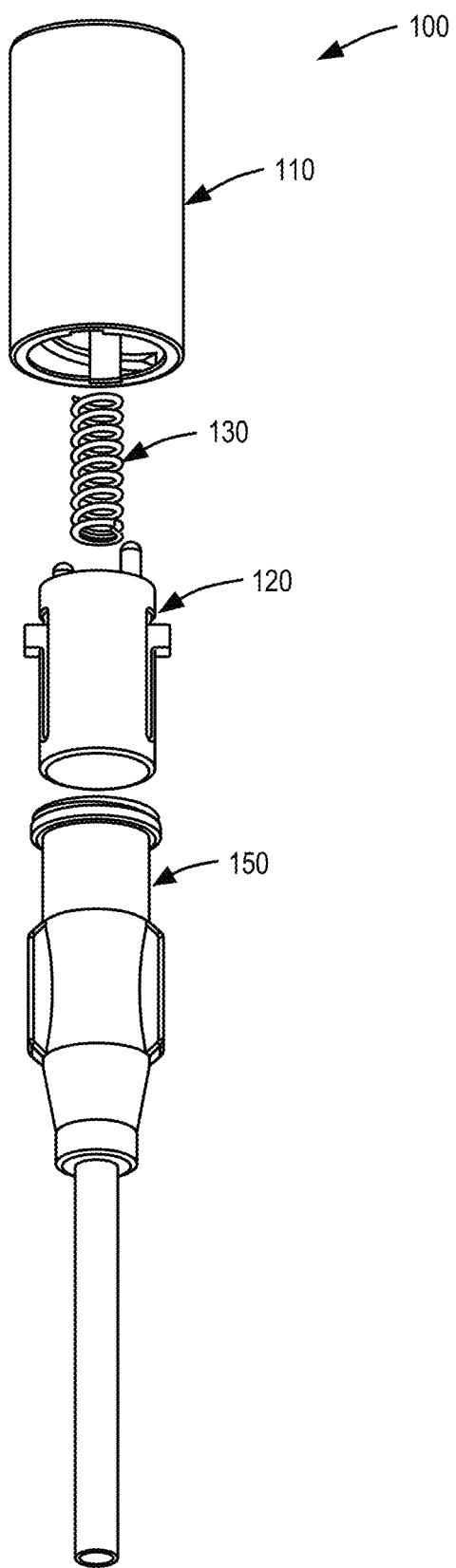
FIG. 4 shows an exploded view of the port protector in embodiments of the present invention.

FIG. 4 shows an exploded view of port protector 100. Port protector 100 has a cap component 110 for enclosing the rest of the components of port protector 100 and for screwing onto the catheter port 150. Port protector 100 also has the aforementioned piston 120 which, when assembled, is retained in cap 110. Port protector 100 also has a compression spring 130 which is installed under compression in the port protector 100's unused state between the cap 110 and piston 120. The spring enables the extension of the piston 120 relative to the cap 110 as described above and other operation to be described below. Spring 130 is captured by a pin in piston 120 and a corresponding void in cap 110.

Figure 5:
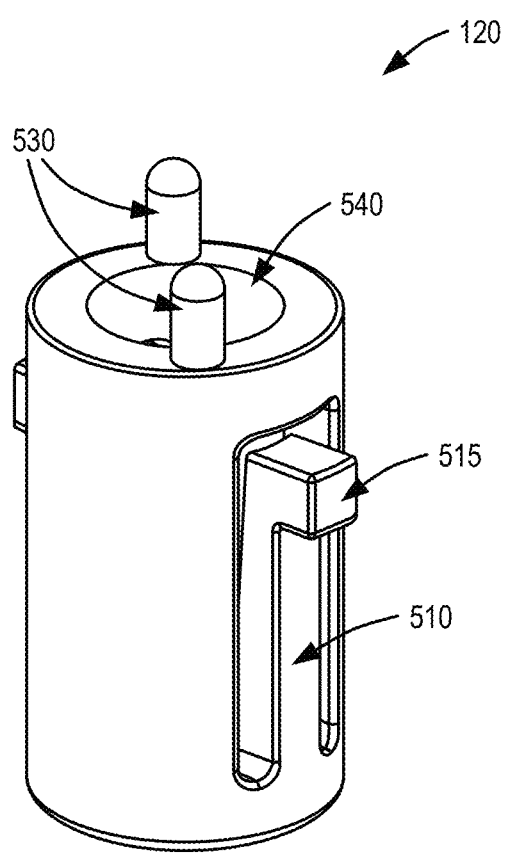
FIG. 5 shows details of a piston of the port protector in embodiments of the present invention.

FIG. 5 shows a more detailed view of the piston 120 in embodiments of the present invention. Piston 120 has a pair of spring fingers 510 which are flush with the surface of piston 120, and are located 180 degrees opposed to one another. Fingers 510 further have tabs 515 at their ends. Fingers 510 are compressed prior to installation of piston 120 in cap 110 and, when so installed, fingers 510 provide tension of tabs 515 against the inner wall of cap 110 and other structures inside. These tensioned tabs 515 then mate with various structures in cap 110 during various modes and operations as will be described below.

Piston 120 further has a hole or void 540 for receiving spring 130. Lastly, piston 120 has two guide pins 530 at the top of piston 120, located 180 degrees opposite from one another. Guide pins 530 ride along surfaces inside cap 110 to rotate the piston 120 relative to cap 110 as described below.

Figure 6:
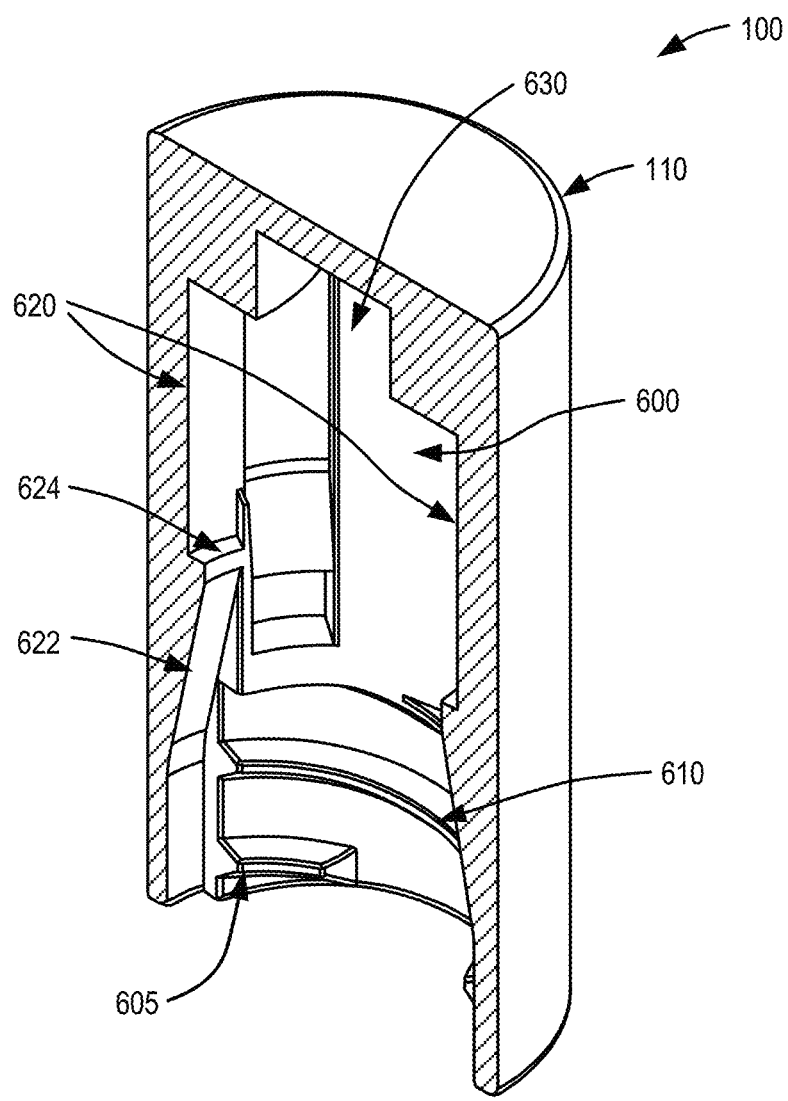
FIG. 6 shows a perspective section view of a cap portion of the port protector in embodiments of the present invention.

FIG. 6 shows a sectional view of cap 110. Cap 110 contains various structures, which mate and interact with those on piston 120. Cap 110 contains a female threaded portion 610 adjacent the opening 605. This allows threading of cap 110 onto a corresponding male thread 155 of catheter port 150 for securely covering the catheter port. Cap 110 has opposing insertion slots 620 on opposite ends of the cap. Slots 620 are for receiving tabs 515 on piston 120 and are kept secured against the slots by the tension of spring fingers 510. Port protector 100 is assembled by lining up tabs 515 to mate with slots 620 and inserting piston 120 into cap 110. As insertion of piston 120 continues, under tension, tabs 515 are guided by and travel along insertion slots 620 in cap 110 and up ramps 622. Once tabs 515 reach the end of the ramps 622, the tabs snap into the edges 624 of ramps 622 and lock piston 120 into the installation configuration shown in FIG. 1. Tabs 515 in this position against edge 624 also prevent removal of piston 120 from cap 100. This insertion completes the assembly of port protector 100 and it is ready for use. Piston 120 resides in its recessed (uninstalled) state as shown in figure—piston 120 can move freely inwardly on cap 110 for installation onto catheter port 150, but cannot be removed from the cap 110.

Figure 7:
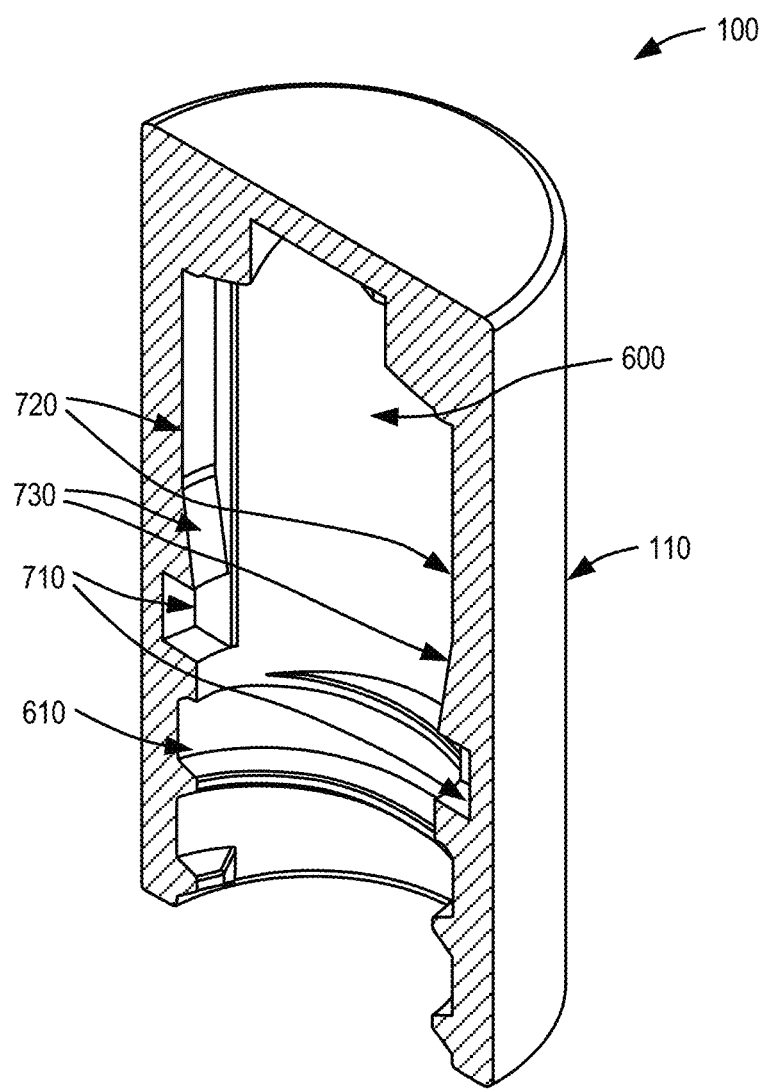
FIG. 7 shows an alternate perspective section view of the cap portion of the port protector in embodiments of the present invention.

FIG. 7 shows a section view of cap 110 when it has been rotated by roughly 20 degrees. This is to more clearly illustrate a second pair of slots 720 called extraction slots. Extraction slots 720 are configured to receive the tabs 515 when the port protector 100 is being removed from catheter port 150. Extraction slots 720 extend all the way down the cap 110 until they end just before threads 610. At the end of slots 720 are pockets 710 for capturing tabs 515 during the extraction operation. Ramps 730 put the spring fingers 510 under additional tension so that when the tabs 515 travel to the end of the ramps in the slots 720, the fingers 510 snap the tabs 515 into pockets 710. Because the pockets 710 have a profile which is complementary to that of the tabs 515, the piston 120 locks into place. In embodiments of the present invention, the piston 120 is locked in an extended manner as shown in FIG. 3. Piston 120 can now move neither inwardly nor outwardly relative to cap 110. The extended locked position of the piston 120 relative to cap 110 makes the port protector 100 no longer usable for covering catheter port 150 since the threads are no longer accessible for mating to catheter port 150.

Figure 8:
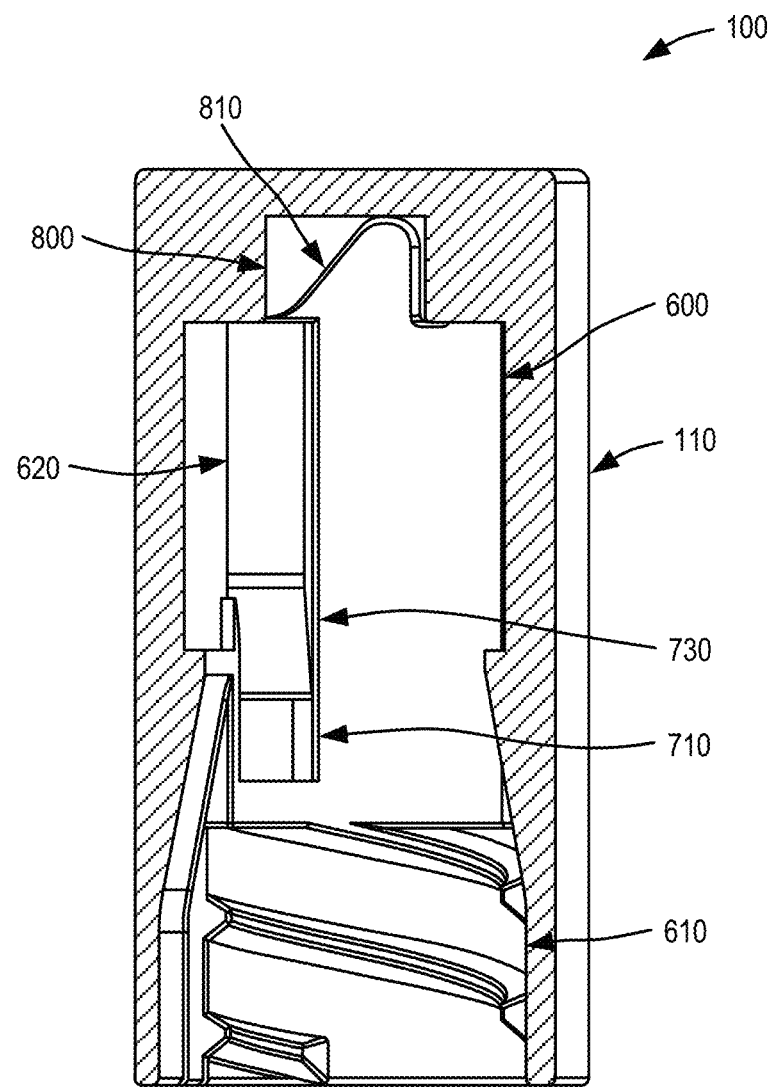
FIG. 8 shows an orthogonal section view of the cap portion of the port protector in embodiments of the present invention.

An orthogonal section view of cap 110 is shown in FIG. 8 to discuss further features of cap 110. At the top of cap 110 above the slots, there is a tubular cavity 800 to retain spring 130. Adjacent the cavity at the top of the inside of the cap 110 are a pair of angular ramps which each run along the wall of the inside of cap 110 and are 180 degrees opposed to one another. During installation of 100 onto catheter port 150, the port 150 pushes the piston 120 farther into cap 110 than the installed state as shown previously. These ramps contact guide pins 530 of piston 120 as piston 120 is completely pushed into the cap 110 by the catheter port 150 during installation of 100 onto 150. As the pins 530 contact ramps 810, the inward motion of piston 120 relative to cap 110 causes the ramps to translate the insertion motion of piston 120 into a rotational motion. Thus, when piston 120 is pushed further into cap 110 during installation, the piston is caused to rotate approximately 20 degrees. This rotation completes upon full installation of port protector 100 onto a catheter port 150.

The rotational motion of piston 120 relative to cap 110 causes the tabs 515 to move from insertion slots 620 to extraction slots 720 when piston 120 reaches the limits of its insertion into cap 110. This prepares the port protector 100 for subsequent removal from catheter port 150 and completion of its single-use mode. Subsequently, when port protector 100 is removed from catheter port 150, piston 120 is pushed out by spring 130 and tabs 515 ride in and are guided by extraction slots 720. As piston 120 travels outwardly from the cap 110 (downwardly in the figure), tabs 515 travel in extraction slots 720. After the tabs ride down ramps 730, tabs 515 then subsequently snap into pockets 710 as previously described. The snapping of the tabs 515 into the pockets 710 thus causes piston 120 to lock into position relative to cap 110. In embodiments of the present invention, piston 120 is locked into an extended position relative to cap 110 to prevent the threads 610 from being accessed a second time and prevent port protector 100 from being re-used. While it is locked in a slightly extended position in described embodiments, any position which prevents re-use of threads 610 is contemplated within the spirit and scope of the present invention.

Figure 9:
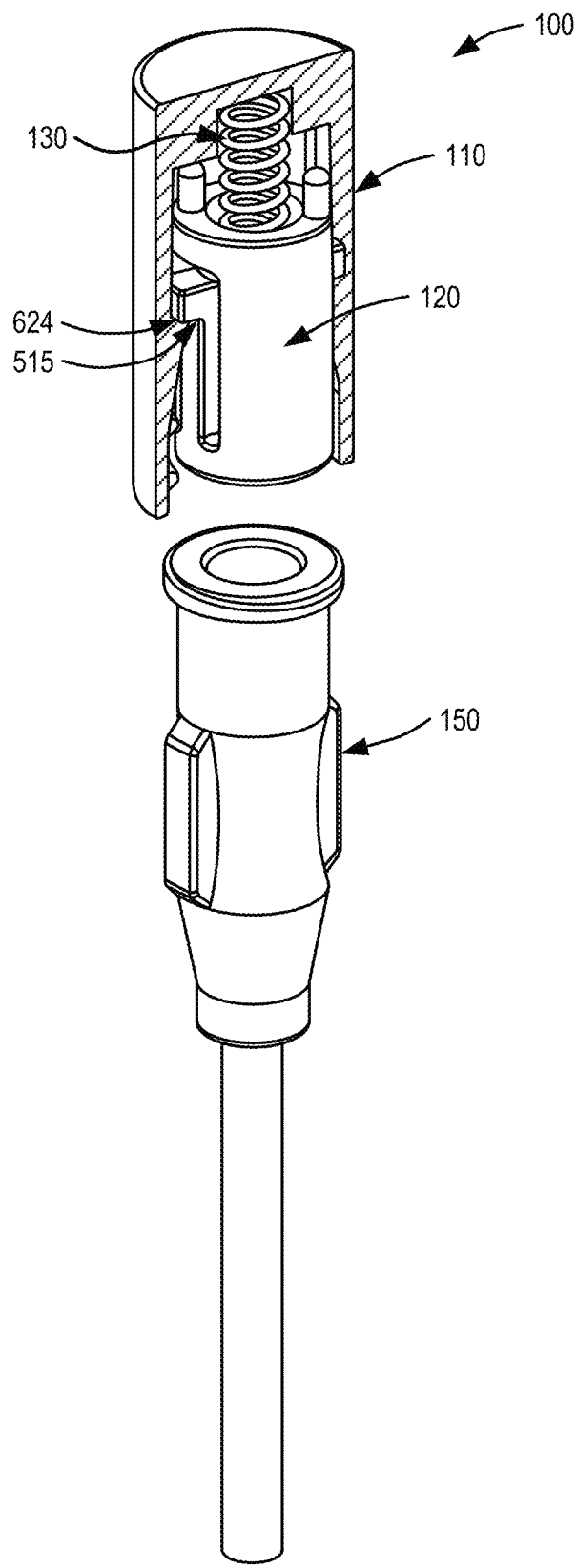
FIGS. 9-14 show various section views of the port protector in operation in embodiments of the present invention.

FIG. 9 shows a section view of port protector 100 in operation to further understand its operation. As in FIG. 1, this shows the unused/uninstalled state of port protector 100. Fully assembled, the tension of spring 130 holds the tabs 515 firmly against the edges 624 of insertion slots 620. As shown, the piston 120 is in a slightly recessed state relative to cap 110 so that catheter port 150 can be aligned with catheter port cover 100 for convenient installation.

Figure 10:
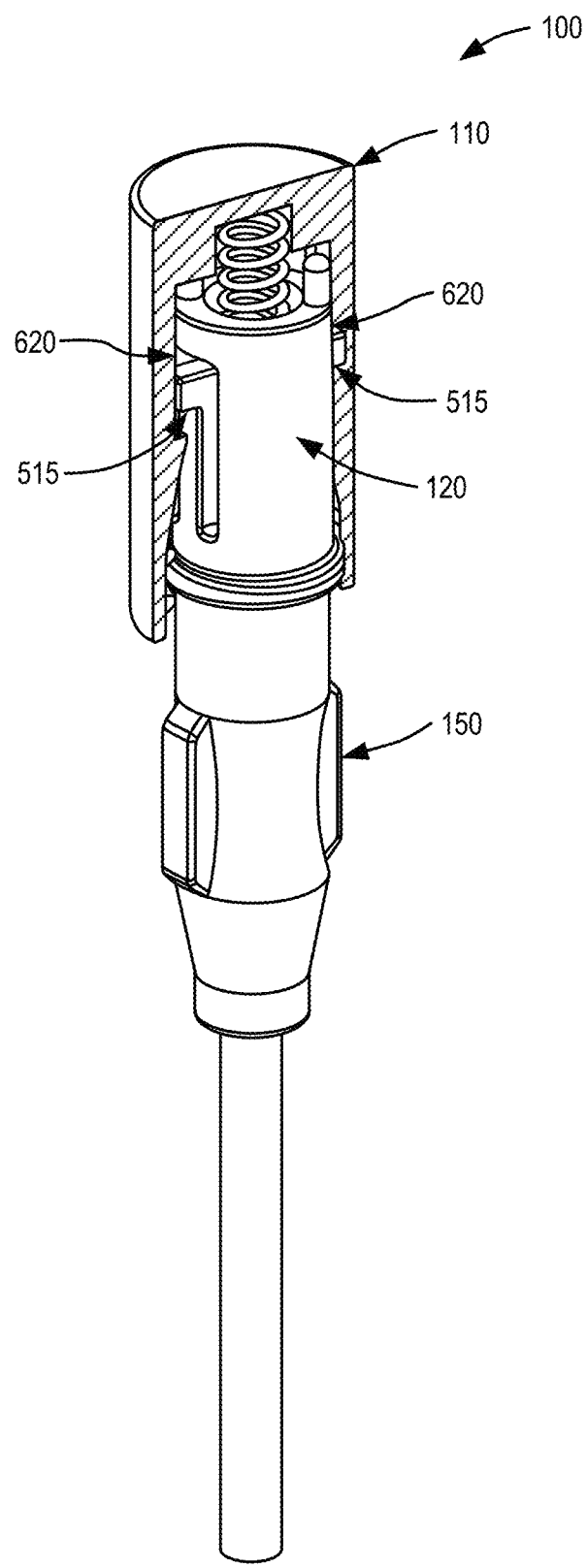

FIG. 10 shows the beginning of the insertion of catheter port 150 into port protector 100. As the catheter port 150 pushes against piston 120 while being threaded, as shown, tabs 515 of piston 120 are sliding along insertion slots 620.

Figure 11:
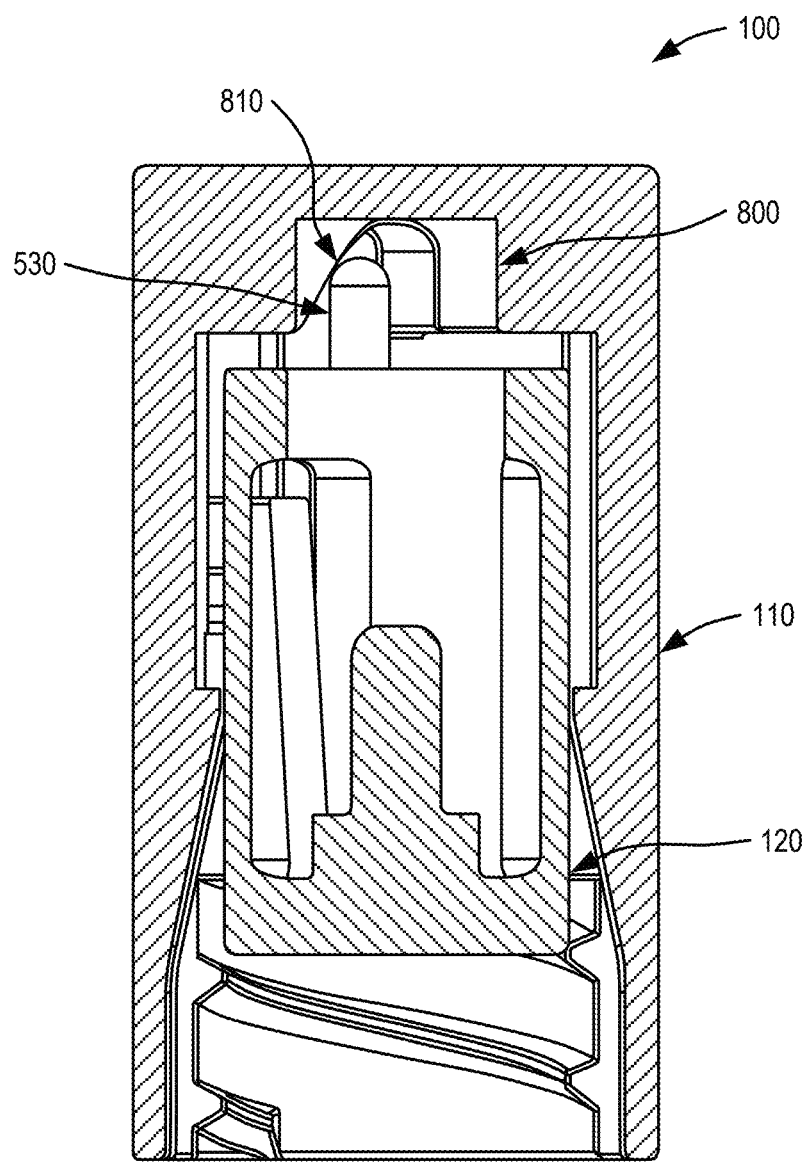

FIG. 11 shows a section view of the state of port protector 100 at a later time during installation when piston 120 slides further into cap 110. Up to now, the piston 120 is at a first angular position relative to cap 110 wherein tabs 515 are guided by slots 620. Guide pins 530 then engage with ramps 810 and further pushing of the piston 120 inwardly relative to the cap 110 causes the rotation of piston 120 inside cap 110 as previously described. This rotation causes piston 120 to reach its second angular position relative to cap 110 so that tabs 515 will engage with the extraction slots 730.

Figure 12:
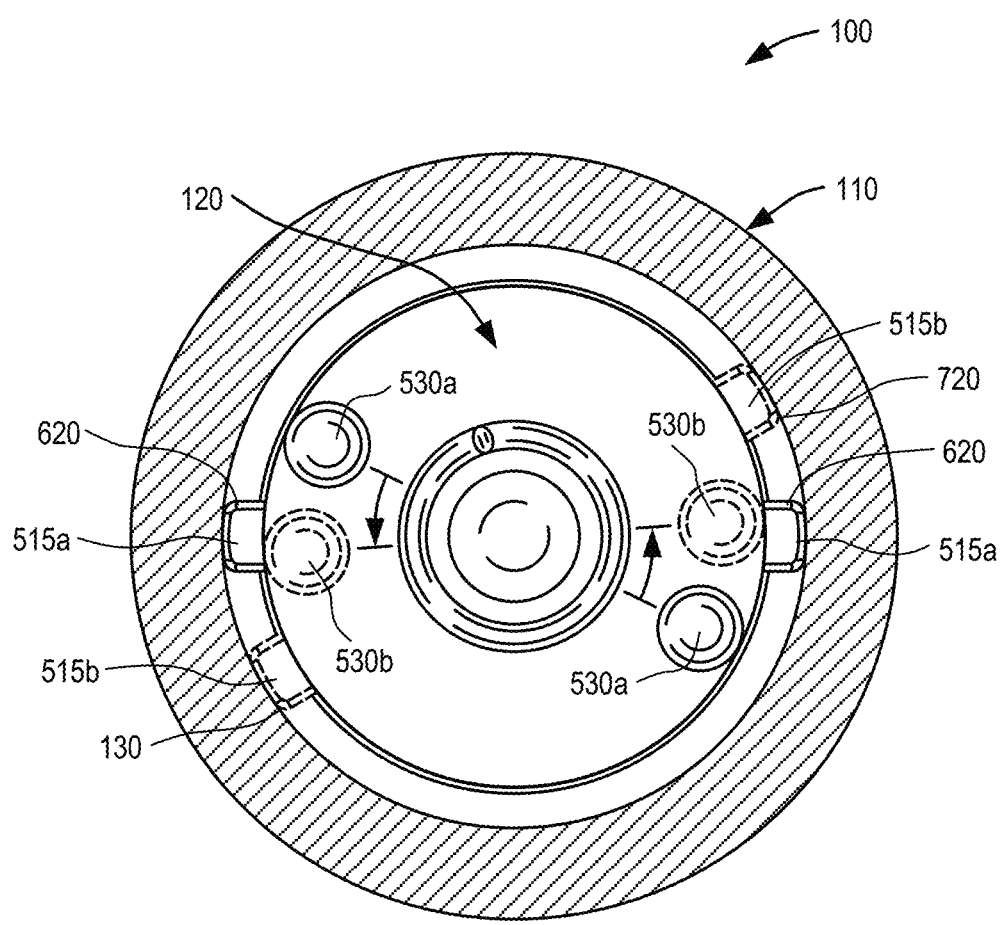

The rotation of piston 120 relative to cap 110 is further illustrated in the top section view of FIG. 12. Guide pins 530 and tabs 515 of piston 120 are shown at first angular or rotational positions 530a and 515a respectively (installation) relative to cap 110. As piston 120 is further pushed into cap 110 by the threading of port protector 100 onto the catheter port 150, due to the interaction of the guide pins 530 and ramps 810, guide pins 530 and tabs 515 rotate to second angular positions 530b and 515b respectively to line tabs 515 up with the extraction slots 720. This prepares the port protector 100 for subsequent removal from catheter port 150 and transition into its "used" state.

Figure 13:
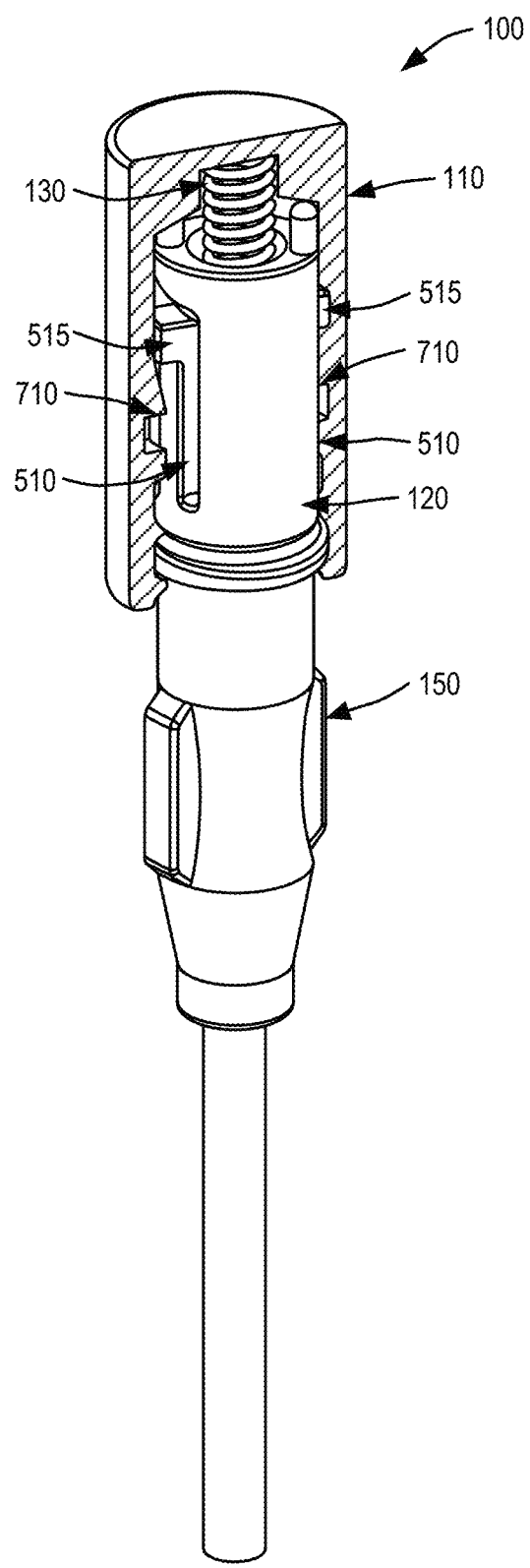

FIG. 13 shows a section view of the port protector 100 after it has been unscrewed from catheter port 150 and is in the process of being uninstalled. As catheter 150 is unscrewed from port protector 100, spring 130, under compression from the installation operation, pushes piston 120 outwardly relative to cap 110 (downwardly in the figure) from the its installed state. Tabs 515 are travelling along extraction slots 720 as catheter port cap 100 is unscrewed from catheter port 150. The tabs 515 will then travel up the ramps 730 and then reach the pockets 710 at the ends of the slots 720 and tabs 515 will snap into the pockets 710.

Figure 14:
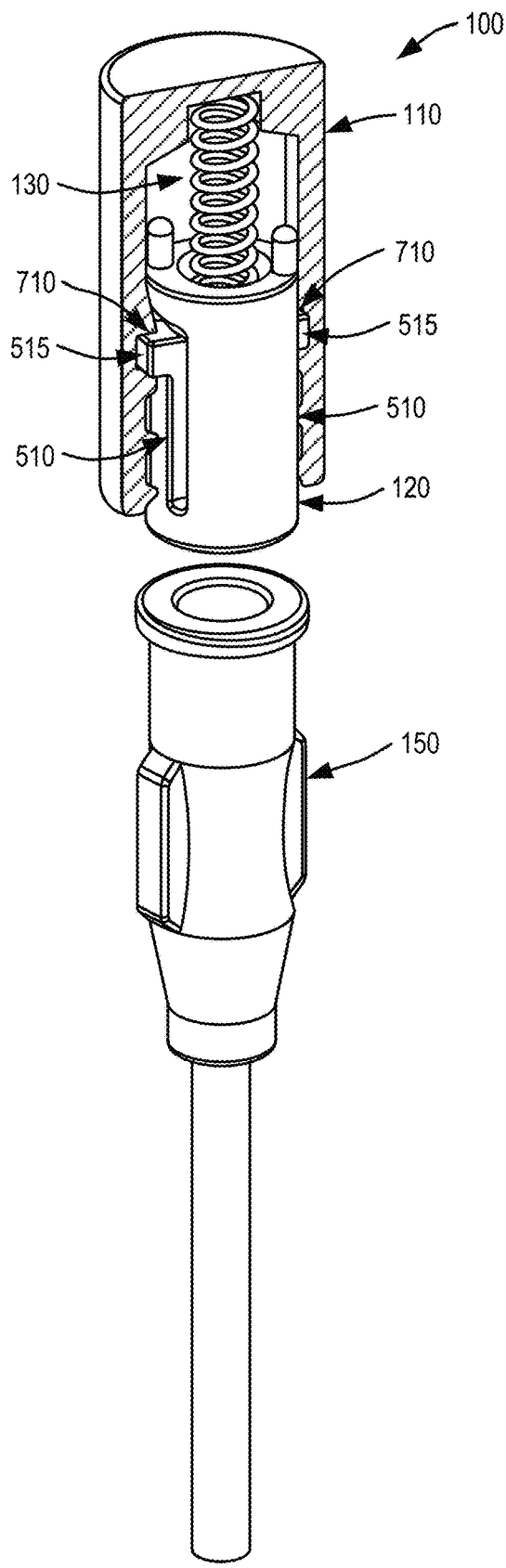

FIG. 14 shows a section view of the port protector 100 after it has been unscrewed from catheter port 150 and completely withdrawn. Tabs 515 have now snapped into the pockets 710 and piston 120 is locked into position relative to cap 110 making the threads 610 inaccessible for subsequent threading onto catheter port 150. Because the threads are now inaccessible, as shown in FIG. 14, the port protector 100 is now no longer usable.

Figure 15:
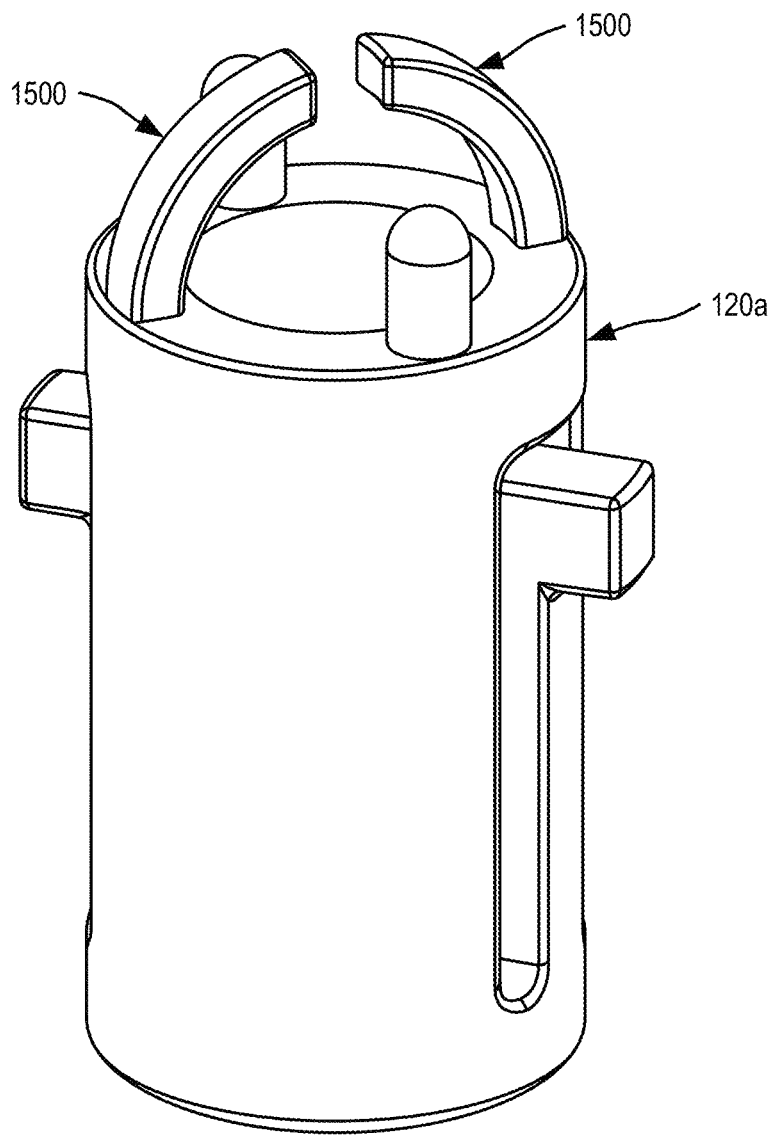
FIG. 15 shows a perspective view of an alternative piston of the port protector in embodiments of the present invention.

FIG. 15 shows an alternative embodiment of the present invention that eliminates the need for spring 130. In this embodiment, instead of a separate spring, piston 120a has an integrated spring implemented as separate molded prongs 1500 on the top of the piston. Alternate piston 120a would operate in all other respects the same as piston 120 and spring 130 in combination as previously described.

Thus, a single-use catheter port protector for catheters has been described. While it has been described with respect to medical applications, and specifically catheters, it is anticipated that such caps may have other applications, where a single-usage or tamper evidence is desirable.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A single-use cap comprising:
   a) a cap for connecting to the inlet or outlet of a container, connector or port for accessing a material;
   b) a piston movably mounted inside the cap;
   c) a first means for retaining the piston at a first unused position with respect to the cap, the first means comprising a tab on the piston and an edge on the cap which mates with the tab to retain the piston at the first unused position;
   d) a means for moving the piston from the first unused position to a second used position within the cap when the single-use cap is connected to and subsequently disconnected from the outlet of the container, connector or port, the means for moving the piston comprising:
      i) a first and second slot on the cap which mates with the tab, the means for moving the tab from the first slot to the second slot when the cap is in operation; and
      ii) a rotation means for imparting a rotational motion onto the piston to move the tab from the first slot to the second slot; and
   e) a second means for permanently retaining the piston in a second used position within the cap, the second used position preventing the single-use cap from being reconnected to the outlet of the container, connector or port.

2. The single-use cap of claim 1 wherein the rotation means further comprises a ramp on the cap and a pin on the piston which, when the piston reaches a first position relative to the cap, causes the pin to contact the ramp and translate an insertion motion into a rotational motion.

3. The single-use cap of claim 1 wherein the means for moving further comprises a means for extending the piston when the single-use cap is uninstalled from the outlet of a container, connector or port.

4. The single-use cap of claim 3 wherein the second means for retaining comprises a lock for locking the piston in an extended state relative to the cap when the single-use cap is disconnected from the outlet of a container, connector or port.

5. The single-use cap of claim 4 wherein the lock comprises a tab on the piston and a pocket on the cap for mating with the tab.

6. The single-use cap of claim 1 wherein the inlet or outlet of container, connector or port is a port on a catheter.

* * * * *